United States Patent [19]

Krag et al.

[11] Patent Number: 4,735,196
[45] Date of Patent: Apr. 5, 1988

[54] CERVICAL-THORACIC ORTHOSIS AND METHOD

[76] Inventors: Martin H. Krag, P.O. Box 424, Rte. 1, S. Hero, Vt. 05486; Levon Pentecost, 1530 Lancaster Ter., Jacksonville, Fla. 32204

[21] Appl. No.: 929,387

[22] Filed: Nov. 10, 1986

[51] Int. Cl.⁴ .......................... A61F 5/02; A61F 5/37
[52] U.S. Cl. ..................................... 128/69; 128/75; 128/76 R
[58] Field of Search ............... 128/69, 75, 78, 68, 128/76 R, 87 B, 84 R, 84 C

[56] References Cited

U.S. PATENT DOCUMENTS

| | | | |
|---|---|---|---|
| 4,968 | 2/1847 | Knapp. | |
| 2,060,173 | 11/1936 | Buschenfeldt | 128/78 |
| 2,474,200 | 6/1949 | McBee | 128/87 |
| 2,706,982 | 4/1955 | Hale et al. | 128/87 |
| 3,336,922 | 8/1967 | Taylor | 128/75 |
| 3,669,102 | 6/1972 | Harris | 128/84 R |
| 3,724,452 | 4/1973 | Nitschke | 128/75 |
| 3,779,549 | 12/1973 | MacNeil | 128/87 B |
| 3,795,040 | 3/1974 | Miller | 128/75 |
| 3,957,040 | 5/1976 | Calabrese | 128/75 |
| 4,194,501 | 3/1980 | Watt | 128/75 |
| 4,299,211 | 11/1981 | Dovnow | 128/89 R |
| 4,383,523 | 5/1983 | Schurman | 128/75 |
| 4,541,421 | 9/1985 | Iversen et al. | 178/87 B |
| 4,620,530 | 11/1986 | Lanier et al. | 128/84 R |

FOREIGN PATENT DOCUMENTS 3302078 7/1984 Fed. Rep. of Germany ........ 128/75

OTHER PUBLICATIONS

Ace Medical Brochure, "Ace Cervical Traction Equipment Including the New Trippi-Wells Tongs and Mark III Halo"—c1981—pp. 1, 10, 12, 13.
"New From Jerome Medical Systems Halo Traction" (p. 3), c1983.
"Halo–Jacket System; A Pictorial Description and Appln. Manual", Durr-Fillauer, c1981—pp. 4, 5 and cover page.
Bremer Orthopedics brochure, "External Fixation for the Cervical Spine"—c1984.
PRM Halo System, brochure, c1984.
Durr-Fillauer brochure—"Halo System".

Primary Examiner—Edgar S. Burr
Assistant Examiner—Tonya Lamb
Attorney, Agent, or Firm—Wood, Herron & Evans

[57] ABSTRACT

Disclosed is a cervico-thoracic orthosis and method for preventing relative motion between the cervical spine and thorax of a patient. The device bears on only certain specific local areas or sites on the surface of the thorax which are part of the thorax itself and which move only minimally relative to it. The device derives no substantial support from any site on the body which is highly movable relative to the thorax. A halo ring for engaging the skull is rigidly supported by the device.

14 Claims, 3 Drawing Sheets

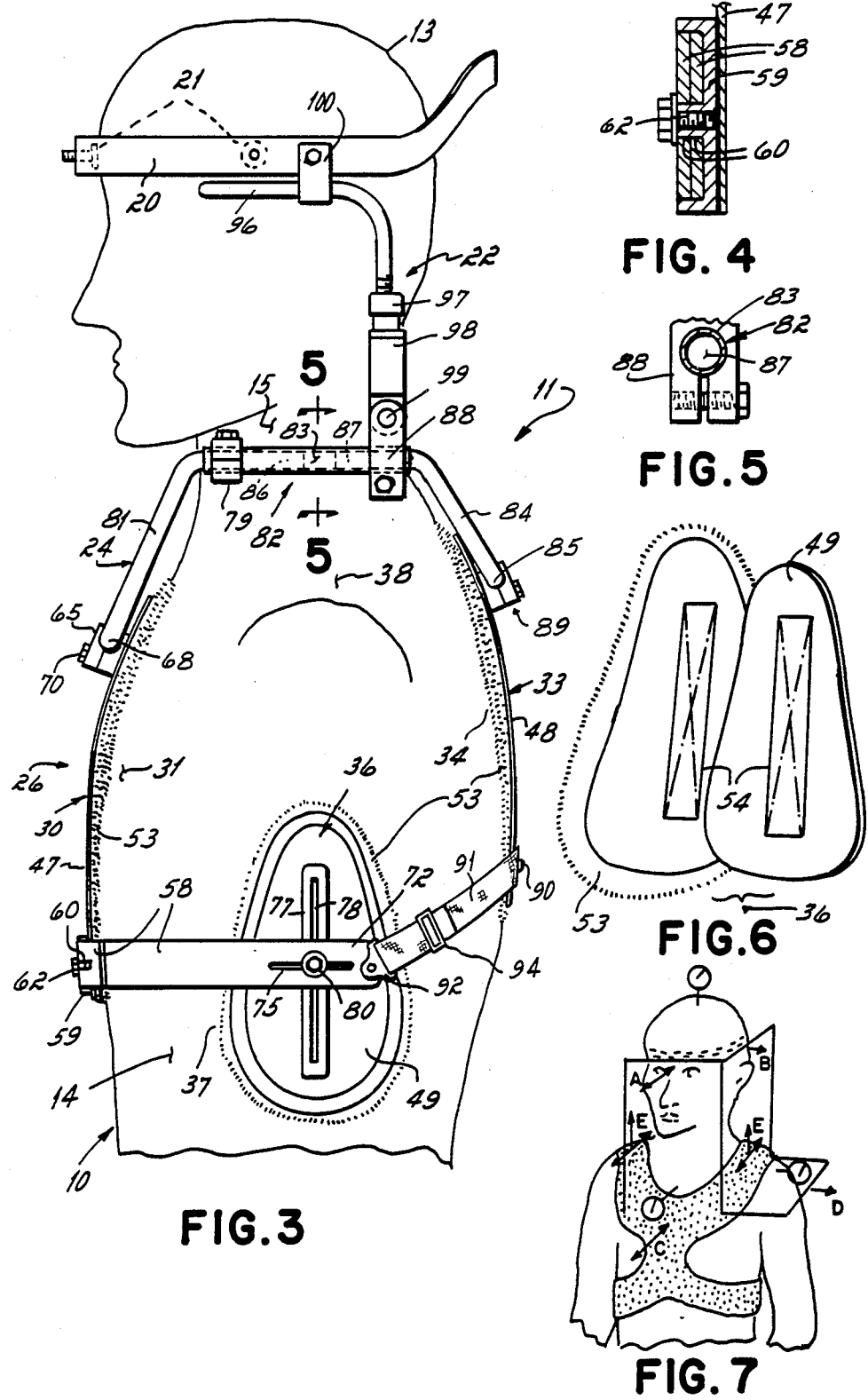

CERVICAL-THORACIC ORTHOSIS AND METHOD

FIELD OF THE INVENTION

This invention relates to a device known as a thoracic orthosis which is used to immobilize the cervical spine of a patient relative to the body.

BACKGROUND OF THE INVENTION

Cervical-thoracic orthoses are known per se and generally comprise (1) a metal ring or "halo" which is secured around the head, as by screws with sharp tips which engage the surface of the skull; (2) a vest-like structure, typically of rigid or semi-rigid material, which tightly surrounds and moves with the upper torso; and (3) rigid connectors such as metal rods which connect the halo to the vest and which permit adjustment of the location of the halo relative to the vest. These devices are used to immobilize the head relative to the thorax, to provide the stabilization which is necessary in the treatment of certain injuries to the neck or upper spine, for example fractures, dislocations, tumors and other causes of mechanical instability or weakening of the vertebrae.

THE PRIOR ART

Prior art halo vests typically include rigid or semi-rigid vests which encircle the body and engage the trunk over a large area, including the upper aspect of the shoulders, i.e., the shoulder girdles; the posterior aspect of the scapula; the pectoralis major muscle and/or breast tissue; and the upper portion of the abdomen. Little if any motion occurs between the vest and the head. However, the prior art vests engage and are at least partially supported on areas of high mobility relative to the thorax such as the pectoralis, breast tissue, abdomen portions, oblique muscles and/or lateral tissue. Because these areas can move relative to the thorax, there can be relatively large motion between the vest and the thorax, so that the cervical spine is not, in fact, immobilized relative to the thorax.

Moreover, the prior art vests are relatively uncomfortable to wear and impose inconveniences because they cover so large a portion of the thorax surface. This also makes them difficult to apply to the patient and difficult to wash under while being worn. Furthermore, they cover the scapula which allows the possibility of scapular spine pressure sores, particularly in spinal cord injured patients.

BRIEF DESCRIPTION OF THE INVENTION

We have invented a cervical thoracic orthosis and a method of stabilization which does not use a vest of the prior art type. The new orthosis bears on the thorax on only certain areas of limited mobility; it does not substantially bear on highly mobile areas of the thorax. This in turn provides substantially better immobilization of the cervical spine relative to the thorax. This highly desirable result is accomplished while at the same time adverse forces are reduced, pressure sores are reduced, cleanliness and comfort are improved, and the device can more easily and quickly be individually fitted to the patient.

More specifically, the orthosis and method of this invention avoid substantial contact with or bearing support from the upper aspect of the shoulder girdle, the posterior aspect of the scapula, the pectoralis major muscle and breast tissue, and the upper portion of the abdomen, that is, the areas which are relatively mobile in position relative to the thorax. Motion of these portions can in fact move (relative to the thorax) an orthosis which derives support from them. We have discovered that a remarkable improvement in stability is achieved by an orthosis which does not derive substantial support from those areas.

In accordance with this invention, the orthosis substantially engages the thorax at only certain areas or sites of contact. By "substantial engagement," as used herein, is meant load bearing contact, as distinguished from merely brushing against, without significant support. These sites are, the anterior aspect of the sternum, the posterior aspect of the interscapular region; and the lateral aspect of the thorax below each shoulder.

The orthosis engages and is supported from these areas through pads which are much smaller in total area than the body-encircling vests of the prior art.

In preferred form, the orthosis is supported through four relatively small thorax-engaging pads. One pad engages the front of the thorax on the anterior aspect of the sternum above the abdomen; another engages the posterior aspect of the interscapular region on the back (between the shoulder blades). Two other pads engage the lateral aspect of the thorax, under the arms. These four pads are secured together by rigid bars or rods which do not themselves substantially engage the body, and by straps by which they are held relatively together so that they encircle, bear against, and derive support from the four areas just identified.

In the preferred form of the invention a rigid arched yoke extends above the shoulders on each side of the neck, and connects the sternal pad in front to the interscapular pad in back. The yoke passes over but is spaced from the shoulders, neck and chest. A rearwardly curving rigid bar or strut is connected between the sternal pad in front and each lateral pad on the sides, but does not engage the abdomen. A flexible posterior strap extends on the back between each lateral pad and the interscapular pad. The halo ring is connected to the shoulder yoke by adjustable connecting bars which extend upwardly above each shoulder.

The invention can best be further described and explained by reference to the accompanying drawings, in which:

FIG. 3 is a lateral view of a patient wearing the orthosis of FIG. 1;

FIG. 4 is an enlarged cross-sectional view taken on line 4—4 FIG. 1;

FIG. 5 is an enlarged cross-sectional view taken on line 5—5 of FIG. 3;

FIG. 6 shows a preferred means of attaching the cushions to the support plates of the orthosis; and FIG. 7 is a diagrammatic perspective of a test subject wearing a generalized type of vest, showing the directions and positions in which various loads were applied to experimentally measure the resulting movement.

Figure 1:
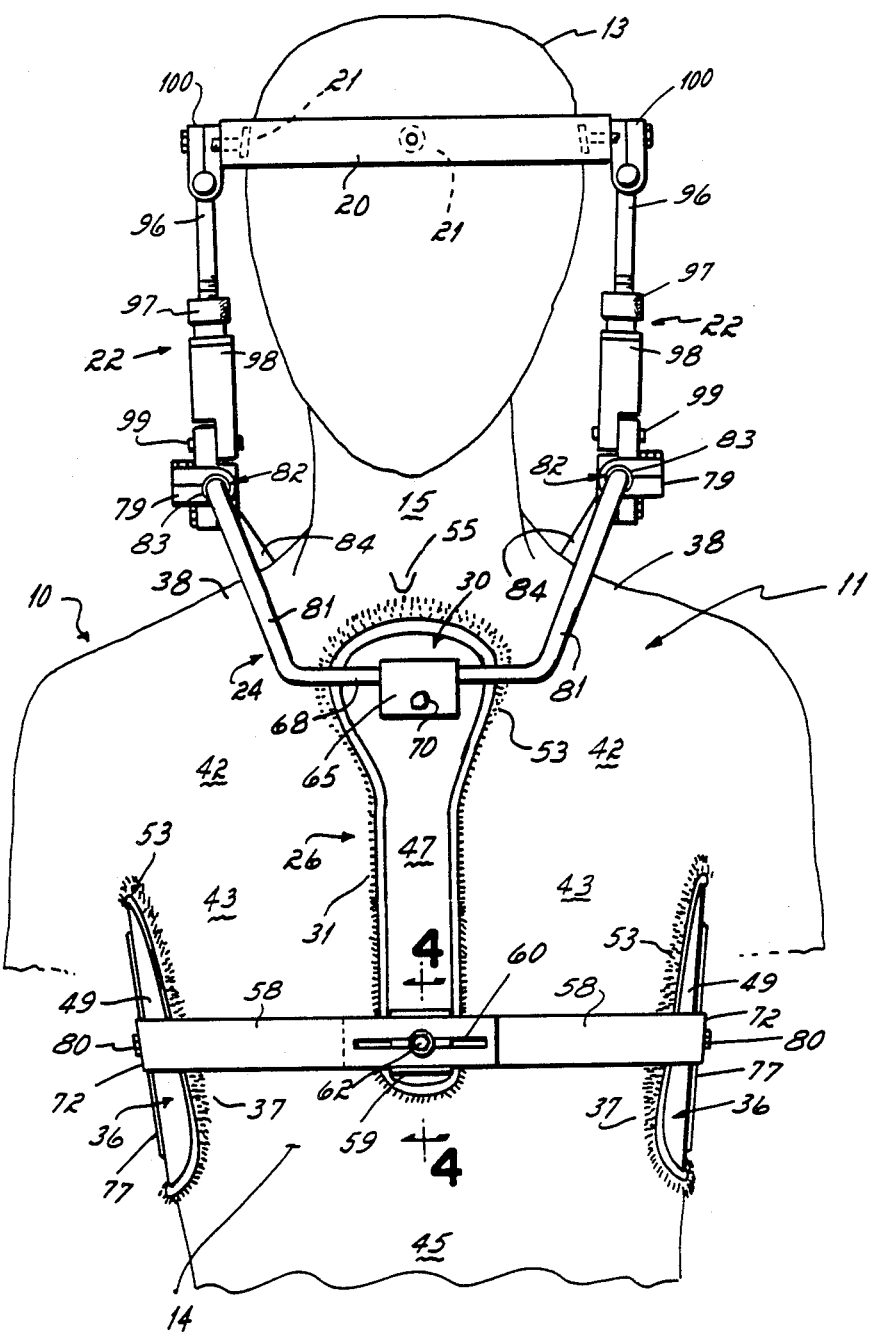
FIG. 1 is an elevation of the anterior (front) aspect of a patient wearing an orthosis in accordance with a preferred embodiment of the invention.
Figure 2:
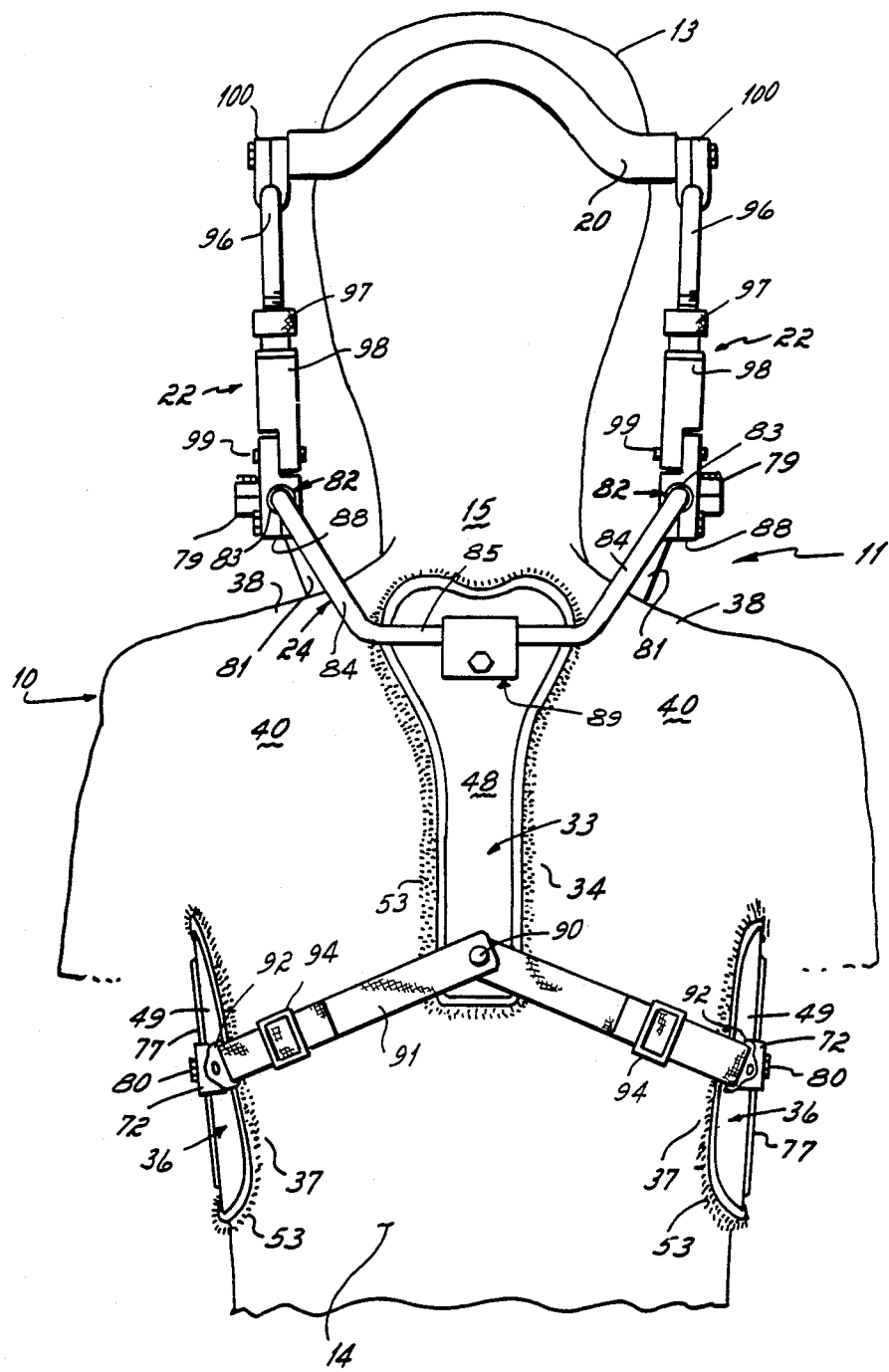
FIG. 2 is a posterior (back) view of a patient wearing the orthosis of FIG. 1.

In FIGS. 1, 2 and 3, a patient 10 is shown wearing an orthosis, designated generally by 11, in accordance with a preferred form of the invention. The function of the orthosis is to immobilize the patient's upper or cervical spine relative to the thorax 14 so that there will be no more than minimal movement of the upper spine.

In the preferred embodiment shown the orthosis 11 comprises four major components, as follows:

a halo ring 20, which engages the head 13, for example by three or more pointed pins such as those designated individually by 21;
  ring connecting means 22, 22 which rigidly secure the ring to the lower portions of the orthosis;
  a shoulder yoke 24 which runs above the patient's shoulders, and from the tops of which the ring connecting means 22, 22 extend; and
  a thorax-engaging portion designated generally by 26.

Halo rings such as that shown at 20 are known per se and do not comprise the invention.

The thorax-engaging portion 26 of the orthosis includes four relatively small pads (in relation to the vests of the prior art) which engage and bear upon the thorax at four discrete, spaced apart positions:

a sternal pad 30 which engages the anterior aspect of the sternum 31 of patient 10 (see FIG. 1);
  on the patient's back, an interscapular pad 33 engages interscapular region 34 between the shoulder blades (see FIG. 2); and
  two lateral pads, each designated as 36, which engage the respective lateral aspects 37 of the thorax at the patient's sides, beneath the arms (see FIG. 3).

It should be noted that thorax-engaging portion 26 bears on the body at these four areas and, just as important, that it does not substantially engage the thorax at other areas. Thus there is no substantial contact between either portion 26 or the shoulder yoke 24 and the upper aspect 38 of the shoulder girdle; nor is there any substantial engagement with the posterior aspect 40, 40 of the scapula (FIG. 2). Further, there is no contact with the pectoralis major muscle 42, nor the breast tissue 43, 43, nor the upper portion 45 of the abdomen (FIG. 1). Each of these non-contacted areas 38 can move relative to the thorax and relative to the four contacted areas 31, 34, 37, and 37. To the extent the orthosis bears substantially on any of the areas 38, 40, 42, 43, or 45, potentially injurious forces or movements can more readily be transmitted from the thorax to the head and then to the neck 15 and the cervical spine.

The four pads 30, 33, 36, 36, have relatively rigid plastic or metal support plates 47, 48, 49, 49, respectively. Each plate mounts a removable cushion of sheepskin or other soft material, one of which is designated by 53, which bears against the respective area of the patient's body. The cushions 53 may be removably secured to the plates by mating hook-and-pile type connectors 54, 54 (see FIG. 6), such as those sold under the trademark Velcro. It is these cushions rather than the plates themselves which engage the patient.

As shown in FIG. 1, sternal pad 30 preferably has an outline shape like that of a downwardly projecting bicycle seat, and its widest portion engages the upper part of the sternum. At the top the pad 30 preferably lies just below the sternal notch 55 of the patient; its lower end is at the lower end of the sternum and does not contact the abdomen. Plate 47 of sternal pad 30 is connected from its lower end to the plates 49, 49 of the lateral pads 36, 36 by rearwardly curving rigid bars, rods or struts 58, 58 (FIGS. 1 and 3). Each strut 58 has a lateral slot 60 at the front, and is adjustably secured in a guide channel 59 of the sternum pad 30. The guide channel 59 (which may be E-shaped in section as shown in FIG. 4) receives the threaded end of a lock bolt 62 which passes through the slot 60 and secures the struts 58 to sternal mount plate 47 so as to confine movement of the lateral pads in the direction of slots 60. This permits each lateral pad 36 to be adjusted inwardly or outwardly, to fit the pads to the breadth of a specific wearer.

Shoulder yoke 24 is secured to sternal plate 47 by means of a split clamp 65. The clamp has a crossbore in which is received the anterior bottom run 68 of the shoulder yoke 24. Clamp 65 secures plate 47 in desired angular rotational position on the bottom run 68 of the yoke, by a locking bolt 70. This adjustment enables the plane or angle of the sternal pad to be adjusted to match that of the sternum area against which it bears.

Each lateral pad 36 is adjustably secured to the rearward end 72 of the respective strut 58 by means which permits the lateral pad to be moved both in the horizontal direction and in the vertical direction (see FIG. 3). For this purpose the end 72 of strut 58 has a generally horizontal slot 75, and the support plate 49 of the lateral pad 36 has a raised rib or boss 77, in which a vertical slot 78 is formed. A lock bolt 80 secures strut 58 to support plate 49. By these means the lateral and vertical positions of the plates 49, 49 can be adjusted.

Yoke 24 includes the anterior bottom run 68, where it is secured to sternal pad 30; upstanding frontal or anterior legs 81, 81; horizontal upper runs 82; posterior legs 84, 84; and a posterior bottom run 85 between the legs 84, 84 (see FIGS. 2 and 3). The yoke may be formed of tubing.

The upper run of 82 on each side of yoke 24 comprises a tube 83 into which the horizontal ends 86 of anterior legs 81 may slide. These ends 86 are adjustably clamped within the tube 83 by split clamps 79. The ends of anterior legs 84 are permanently fixed in the tube 83.

On the back of the apparatus, as shown in FIG. 2, the interscapular pad 33 includes a support plate 48 which again is preferably shaped rather like an elongated bicycle seat. Its upper end preferably is just below $C_7$ vertebrae of the spine. It is adjustably connected to the posterior bottom run 85 of shoulder yoke 24, as by an interscapular split clamp 89 which may be similar to the sternum split clamp 65 previously described. By means of this clamp 89 the interscapular pad 33 can be rotationally adjusted to fit the angulation of the interscapular site 34. (In the preferred embodiment the yoke extends over the shoulders, but it should be noted that the yoke can alternatively pass under the arms, to connect the various members.)

Interscapular pad 33 preferably extends from the base of the neck downwardly over at least the upper portion of the thoracic spine. A flexible web or strap 91 is secured at 90 to the lower end of interscapular support plate 48. The outer ends of strap 91 pass through quick release buckles 92, 92, secured at the rearward ends 72 of the bars 58, 58, and are secured by quick acting clamps 94, 94, so that the pads 49, 49 may be drawn inwardly. The straps may engage the body, but no substantial support is derived from those areas of contact.

Halo ring 20 is generally oval in plan and is sized to encircle the head, and is secured to the skull by pointed screws 21. This ring is supported above and locked rigidly to yoke 24 by ring connecting means 22, 22 on opposite sides of the neck. Each connector includes an L-shaped upper portion 96 (FIG. 3), the lower end of which is adjustably secured as by a lock nut 97 in a sleeve 98. The lower end of sleeve 98 is rotationally fixed as at 99 to the rear clamp 88, which is in turn clamped to the upper run 82. The horizontal upper end of leg 96 mounts a split clamp 100 through which it is adjustably secured to the halo ring 20.

COMPARATIVE TESTS

In order to quantify the effectiveness of the apparatus of this invention in comparison to prior art orthosis, the various devices were worn one at a time by each of seven normal volunteers, and were subjected one at a time to each of the nine load types. FIG. 7 shows a generalized form of orthosis and the positions and directions of the different load types applied to each test subject wearing it. Load types, A, B, C and D, in the directions and positions shown in the drawing, were applied manually with loads gradually increasing from 1 to 10 pounds, as measured by a strain gauge. The resulting displacements were monitored by either photogrammetry (load types A and B, and rotation angles) or extensometer (load types C and D). Load types E were applied by the subject moving his scapulae maximally anteriorly, posteriorly or cephalad, with displacements monitored by an extensometer.

For each type of displacement, for each subject:
(a) the data for the orthosis were normalized against an index;
(b) the mean of the normalized values was calculated across the subjects; and
(c) rank ordering was performed, and an overall score was defined as the mean of the rank order number, averaged across the nine load types.

The results are shown in the following table:

| COMPARISON OF MOBILITY ON THORAX FOR DIFFERENT ORTHOSES | | | | | | | | | |
|---|---|---|---|---|---|---|---|---|---|
| | Load Type | | | | | | | | |
| Device | ant. A | post. A | B | ant. C | post. C | D | ant. E | post. E | ceph. E | Avg. Score |
| 1. | 8 | 7 | 7 | 4 | 6 | 7 | 8 | 8 | 7 | 6.88 |
| 2. | 5 | 4 | 6 | 5 | 8 | 8 | 4 | 3 | 8 | 5.67 |
| 3. | 6 | 3 | 8 | 7 | 5 | 6 | 2 | 2 | 2 | 4.56 |
| 4. | 3 | 6 | 4 | 3 | 2 | 5 | 6 | 6 | 5 | 4.44 |
| 5. | 2 | 2 | 2 | 6 | 4 | 2 | 7 | 7 | 6 | 4.22 |
| 6. | 4 | 8 | 1 | 8 | 1 | 3 | 5 | 5 | 3 | 4.22 |
| 7. | 7 | 5 | 5 | 2 | 3 | 4 | 3 | 4 | 4 | 4.11 |
| 8. | 1 | 1 | 3 | 1 | 7 | 1 | 1 | 1 | 1 | 1.89 |

Vest 1 was a vest sold by DePuy of Warsaw, IN.
Vest 2 was a "JMS" vest sold by Jerome Medical System, Inc. of Mt. Laurel, New Jersey.
Vest 3 was a "PMT-Patil" vest sold by PMT Corporation of Minneapolis, MN.
Vest 4 was an "Ace" vest sold by Ace Orthopedic Mfg. Co. of Los Angeles, CA.
Vest 5 was a "Camp" vest sold by Camp International Inc. of Jackson, MI.
Vest 6 was a "Pope" vest sold by Pope Brace Company of Greenwood, S.C.
Vest 7 was a "Bremer" vest sold by Bremer Orthopedics Corp. of Jacksonville, Florida.
Device 8 was in accordance with this invention.

As can be seen, the device of the present invention had an overall average score of 1.89, far better than that of the next best. Indeed, the present device scored best for 7 of the 9 load types. Its seventh rank position for the load type C (posterior) was due to displacement of one subject which was markedly different than for any of the other three subjects.

Thus it can be seen that the device of this invention provides extremely good immobilization. Moreover, the device is light in weight, cool to wear, and minimizes risk of development of scapular pressure sores.

The cushions are easy to change and easy to wash under.

Having described the invention, what is claimed is:

1. A cervical-thoracic orthosis for minimizing relative motion between the head and thorax of a patient, and thus of the cervical spine, said orthosis comprising,
   a sternal pad for bearing against the anterior aspect of the sternal site of the patient;
   an interscapular pad for bearing against the posterior aspect of the interscapular region of the patient; and
   two lateral pads for bearing against the respective lateral aspects of the thorax beneath the arms of the patient,
   support means interconnecting said pads; and
   means for connecting said support means to a halo ring,
   said orthosis making no substantial engagement with the thorax of the patient except through said pads, said orthosis having no structure which substantially contacts the upper aspect of the shoulder girdle, the posterior aspect of the scapula, the pectoralis major muscle and breast tissue, or the upper portion of the abdomen of the patient, said orthosis thereby minimizing the possibility that movement of any of such non-contacted areas relative to said pads could apply undesirable forces to the head and neck, and thus permitting less relative motion between the head and the thorax than a device deriving substantial support from other areas of the thorax than those engaged by said pads.

2. The orthosis of claim 1 wherein each said lateral pad is shaped to bear on the patient's body substantially only on the respective lateral aspect of the thorax.

3. The orthosis of claim 1 wherein said support means comprises,
   an arched rigid yoke extending over the shoulders on each side of the neck, between the sternal pad and the interscapular pad, said yoke passing over each shoulder but spaced from the shoulder, neck and chest,
   a rigid rearwardly curving strut connecting the sternal pad and each lateral pad, and
   a posterior strap extending from each lateral pad to the interscapular pad.

4. The orthosis of claim 3 wherein the halo ring connecting means extends between the yoke and the halo ring.

5. The orthosis of claim 1 wherein said sternal pad bears on the patient's body substantially only on the sternum.

6. The orthosis of claim 5 wherein said sternal pad has a relatively wide upper portion positioned to bear upon the patient's body on the upper portion of the anterior aspect of the sternal site, and a relatively narrow lower portion for bearing upon the lower part of the sternal site.

7. The orthosis of claim 1 wherein said interscapular pad bears on the patient's body substantially only on the posterior aspect of the interscapular region.

8. The orthosis of claim 7 wherein said interscapular pad has a relatively wide upper portion positioned to bear upon the patient's body on the upper portion of the interscapular region, and an elongated relatively narrower lower portion for bearing upon the lower part of the interscapular region.

9. An orthosis for minimizing relative motion between the head and thorax of a patient, said orthosis comprising discrete, spaced support pads which are positioned to engage and be supported only on fixed sites of the thorax surface which are a part of the thorax, said fixed sites comprising the anterior aspect of the sternum, the posterior aspect of the interscapular region, and the two lateral aspects of the thorax;

connecting means for holding said support pads in engagement with said fixed sites, and means for mounting a halo ring on said connecting means;

said orthosis not being substantially supported on areas of the body surface which are movable relative to the thorax and having no structure which substantially contacts the upper aspect of the shoulder girdle, the posterior aspect of the scapula, the pectoralis major muscle and breast tissue, or the upper portion of the abdomen.

10. A method of stabilizing the cervical spine of a patient against movement, comprising, supporting an orthosis on the patient by substantially engaging it with only the following sites on the patient's thorax:

the anterior aspect of the sternal site;

the posterior aspect of the interscapular region; and the two lateral aspects of the thorax;

securing said orthosis on the patient so that it bears only on said sites and moves only as said sites move, spacing said orthosis outwardly from the following areas of the body surface which are movable relative to the thorax:

the upper aspect of the shoulder girdle, the posterior aspect of the scapula, the pectoralis major muscle and breast tissue, and the upper portion of the abdomen;

securing a halo ring around the head of a patient, and rigidly connecting said halo ring to said orthosis.

11. The method of claim 10 further wherein said orthosis bears on the sternal site through a pad having a relatively wide upper portion engaging the upper portion of the sternal site and a relatively narrow lower portion bearing on the lower part of the sternal site and which does not bear upon the pectoralis major muscle or breast tissue.

12. The method of claim 10 wherein said orthosis bears on the interscapular site through a pad having a relatively wide upper portion bearing just below the C7 vertebrae of the spine, and a relatively narrower lower portion bearing upon the lower part of the interscapular region.

13. The method of claim 10 wherein said orthosis is engaged with said patient by pads which engage only said sites.

14. The method of claim 13 wherein said pads are fixed relative to one another by interconnecting struts and straps which extend between them.

* * * * *